US006823716B2

(12) United States Patent
Kelner et al.

(10) Patent No.: US 6,823,716 B2
(45) Date of Patent: Nov. 30, 2004

(54) DEVICE FOR PRECISION MEASUREMENT OF SPEED OF SOUND IN A GAS

(75) Inventors: Eric Kelner, San Antonio, TX (US); Ali Minachi, San Antonio, TX (US); Thomas E. Owen, Helotes, TX (US); Marion Burzynski, Jr., Converse, TX (US); Steven P. Petullo, Fairfax, VA (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 10/406,518

(22) Filed: Apr. 3, 2003

(65) Prior Publication Data

US 2004/0093948 A1 May 20, 2004

Related U.S. Application Data

(60) Provisional application No. 60/427,099, filed on Nov. 18, 2002.

(51) Int. Cl.[7] ........................ G01N 29/18; G01N 29/02; G01N 29/24
(52) U.S. Cl. ........................................ 73/24.06; 73/597
(58) Field of Search .................. 73/1.03, 19.03, 73/23.21, 24.01, 24.02, 24.05, 24.06, 597, 1.82, 1.86

(56) References Cited

U.S. PATENT DOCUMENTS

| 4,567,770 A | * | 2/1986 | Rumbold et al. ............. 73/644 |
| 4,571,693 A | * | 2/1986 | Birchak et al. ............. 364/509 |
| 4,909,080 A | * | 3/1990 | Kikuta et al. ............. 73/290 V |
| 4,938,066 A | * | 7/1990 | Dorr ............................ 73/597 |
| 4,991,976 A | * | 2/1991 | Byles .......................... 374/135 |
| 5,461,931 A | * | 10/1995 | Gill ........................ 73/861.28 |
| 5,526,699 A | * | 6/1996 | Dorr ....................... 73/861.28 |
| 5,581,014 A | * | 12/1996 | Douglas .................... 73/24.01 |

FOREIGN PATENT DOCUMENTS

| WO | 99/67649 | * 12/1999 | ......... G01N/290/00 |
| WO | WO 02/44662 A1 | * 6/2002 | ............. G01F/1/66 |

OTHER PUBLICATIONS

International Search Report for PCT/US 03/36034, 5 pages.*

* cited by examiner

Primary Examiner—Hezron Williams
Assistant Examiner—Rose M. Miller
(74) Attorney, Agent, or Firm—Baker Botts L.L.P.

(57) ABSTRACT

A sensor for measuring the speed of sound in a gas. The sensor has a helical coil, through which the gas flows before entering an inner chamber. Flow through the coil brings the gas into thermal equilibrium with the test chamber body. After the gas enters the chamber, a transducer produces an ultrasonic pulse, which is reflected from each of two faces of a target. The time difference between the two reflected signals is used to determine the speed of sound in the gas.

18 Claims, 5 Drawing Sheets

DEVICE FOR PRECISION MEASUREMENT OF SPEED OF SOUND IN A GAS

RELATED PATENT APPLICATION

This application claims the benefit of U.S. Provisional Application No. 60/427,099, filed Nov. 18, 2002 and entitled "Device for Precision Measurement of Speed of Sound in a Gas".

GOVERNMENT LICENSE RIGHTS

The U.S. Government has a paid-up license in this invention and the right in certain circumstances to require the patent owner to license others on reasonable terms as provided for by the terms of Contract No. DE-FC21-96MC33033 for the U.S. Department of Energy.

TECHNICAL FIELD OF THE INVENTION

This invention relates to the field of ultrasonic measurements, and more particularly, to a device for measuring the speed of sound in a gas using transit time of an ultrasonic pulse.

BACKGROUND OF THE INVENTION

A unique physical characteristic of any gas is the speed of sound through that gas at specified pressure and temperature conditions. This characteristic, in combination with the temperature and pressure of the gas, may be used as a direct testing method for identifying individual pure gases and, further, may serve as one of several measurable physical parameters by which certain gas mixtures containing two or more known gas constituents may be quantitatively analyzed in terms of their concentrations. Application of speed of sound measurements in gases important to the natural gas industry is one in which the speed of sound, in combination with the gas temperature, pressure, and the amount of non-hydrocarbon diluent gases such as carbon dioxide and nitrogen, may be used to experimentally characterize the gas and infer the heating value energy content of the gas. In this application, the natural gas mixture normally contains methane as the primary hydrocarbon constituent (typically in the range of about 90–98 percent by volume concentration) together with variable small or trace amounts of heavier hydrocarbons (ethane through decane) plus carbon dioxide and nitrogen diluent gases at a total concentration in the range of a few percent by volume. Thus, with sensing techniques capable of indicating the gas temperature, pressure, speed of sound, carbon dioxide concentration, and nitrogen concentration, the heating value of the gas may be determined. See Morrow, T. P., Kelner, E. P., and Minachi, A. [20001]. "Development of a Low Cost Inferential Natural Gas Energy Flow Rate Prototype Retrofit Module," Final Technical Report, DOE Cooperative Agreement No. DE-FC21-96MC33033, Southwest Research Institute, San Antonio, Tex. In particular, this method of determining the energy content of natural gas does not require any additional information or measurements defining the hydrocarbon constituents or their concentrations. However, in order to determine the gas heating value to within an accuracy of ±0.1 percent as an acceptable value for gas tariff pricing and custody transfer, the measured parameters, including the speed of sound in the gas, must be determined to within approximately the same or a better degree of accuracy. Therefore, for this application a precision speed of sound sensor becomes an important component of an on-line natural gas energy flow meter. This sensor must operate reliably and accurately to provide the desired precision measurements under a wide range of field installations and ambient conditions and be capable of handling a full practical range of gas compositions common to the natural gas industry. The invention described herein refers to a methodology and apparatus for achieving speed of sound measurements with the desired high precision and reliability for applications associated with the natural gas industry and with users of natural gas. This method will also be recognized as having application in other speed of sound measurements, including tests in other gas compositions, in which high-accuracy results must be obtained.

One approach to measuring the speed of sound in gas involves measurement of the transit time of an ultrasonic pulse traveling over a known propagation distance in the gas. This technique typically employs one or more piezoelectric transducers to generate and detect sound waves in the frequency range of about 20 kHz to 1 MHz and higher. A particular technique known as a "pulse echo" technique uses a single transducer as both the transmitter and the receiver. The generated sound wave is reflected back to the source transducer from a target located at a known distance from the transducer, and is received by the same transducer. If the distance between the transducer and the reflecting target is D, and the measured two-way travel time is t, then the speed of sound is represented by:

$$V_{gas}=2D/t. \qquad (1)$$

This method is advantageous because it uses only one transducer. However, in applications requiring high-precision speed of sound measurements, the method has the disadvantage of introducing time delay errors associated with imperfectly defined and variable distance, D, and an imperfect ability to determine the exact time delay with respect to the time of initiation of the transmitted pulse and the time instant when the reflected sound wave is received at the transducer.

To reduce the time delay error, the pulse echo method may be modified to measure a time difference between two received signals. A transmitted wave is reflected from two different targets rather than a single target. The distance, d, between the two targets is known. Using this method, the speed of sound is represented by:

$$V_{gas}=2d/\Delta t, \qquad (2)$$

where $\Delta t$ is the time difference between the two received signals.

With this two-reflector method, the two ultrasonic wave pulses returning to the transducer will be similar in amplitude and in waveform so that they may be accurately compared and their relative two-way travel time delay, $\Delta t$, measured. In particular, a method of cross correlation analysis may be used as the means for accurately comparing the two reflected pulses in a statistical sense and, in so doing, determine with good accuracy their relative time delay.

Regarding high-precision time-of-flight measurements, the disadvantage related to distance, D, in the single-reflector method is associated with the inability to accurately specify where, near the immediate face of the transmit-receive transducer, the sound wave is initiated in the gas and detected on reflection. More precisely, when the active face of the transducer and the face of the reflector do not have the same material, surface texture and finish, and acoustic impedance, the effective sound wave propagation path length may differ acoustically from the physically measured separation distance. Furthermore, the distance, D, will vary with temperature because of thermal expansion effects in the mounting structure holding the transducer and the reflector. Consequently, the single-reflector pulse-echo measuring arrangement must be calibrated as a function of temperature and appropriate temperature measurements of the mounting structure must be incorporated as part of the speed of sound measurement system.

DETAILED DESCRIPTION OF THE INVENTION

Figure 1:
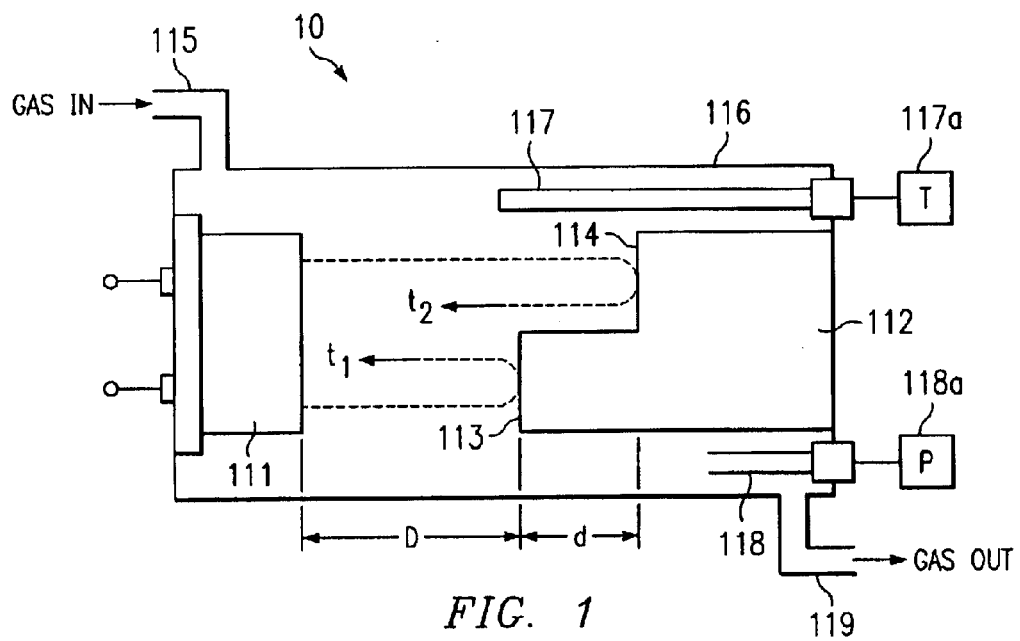
FIG. 1 shows the basic arrangement of the speed of sound sensor using the two-reflector technique in accordance with the invention.
Figure 2:
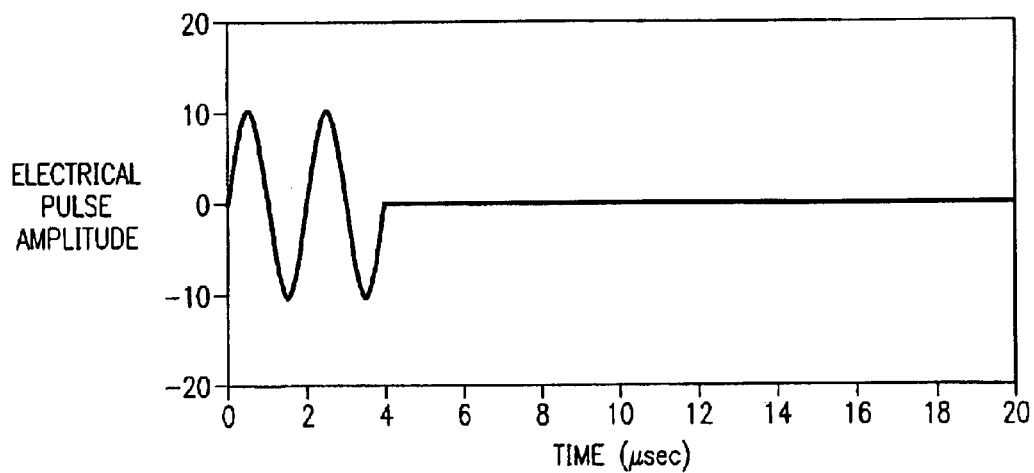
FIG. 2 shows a typical electrical excitation voltage pulse applied to the ultrasonic transducer.
Figure 3:
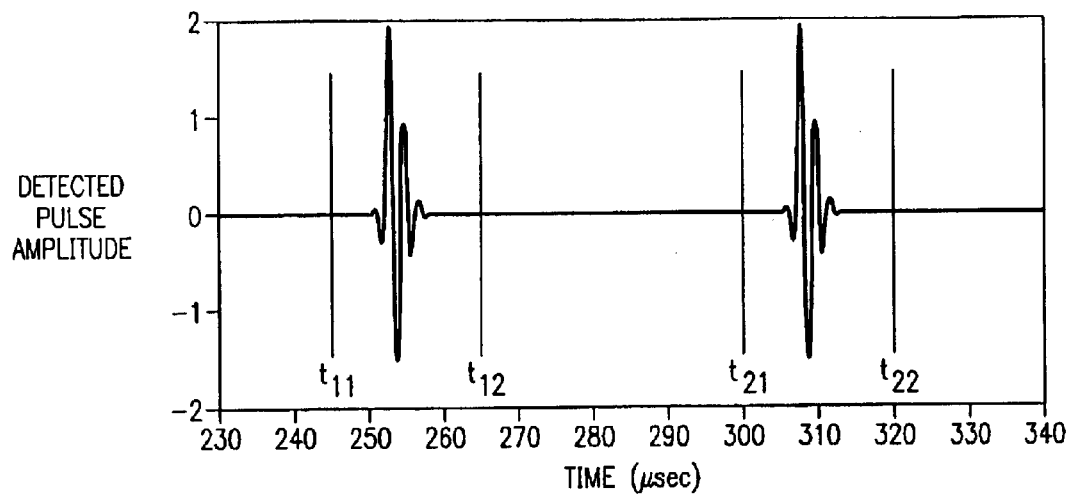
FIG. 3 shows the two ultrasonic pulses reflected from the dual-face target.

FIG. 1 illustrates the basic two-reflector transit time speed of sound sensor 10 in diagramatic form in accordance with the invention. The essential components of sensor 10 are the speed of sound chamber 116, the ultrasonic transmit-receive transducer 111, and the two-reflector target block 112. FIG. 2 illustrates a typical excitation voltage waveform applied to the transmit-receive transducer 111 to produce the transmitted ultrasonic pulse in the gas. FIG. 3 illustrates the two ultrasonic pulses after propagating to and reflecting from the target block 112 and being detected by the transmit-receive transducer 111. In general, sensor 10 and the transducer 111 and target block 112, comprising the primary components of sensor 10, are cylindrical in shape, having a common axis of assembly.

In operation, as further explained below, sensor 10 is capable of yielding precision measurements of the speed of sound in gas and vapor mixtures such as those comprising natural gas. It accepts a flowing stream of gas at gas inlet 15 previously brought to thermal equilibrium with the temperature of the test chamber 116, and measures the gas temperature by means of temperature sensor 117 located within chamber 16 and temperature transmitter 117a and the gas pressure by means of pressure sensor 118 in direct fluid communication with chamber 116 and pressure transmitter 118a, and provides for exit of the gas at gas outlet 119. The transmit-receive transducer 111 is mounted at one end of the cylindrical test chamber 116 with its active face exposed to the gas contained within the chamber 116. The electrical leads of transducer 111 brought out of the chamber 116 via pressure-sealed electrical feedthrough terminals to maintain the pressure integrity of the chamber 116. The reflector target block 112 is made from one piece of material to provide two planar semicircular reflecting surfaces 113 and 114 accurately separated by a distance, d, along the axial length of test chamber 116 and oriented parallel to the face of transducer 111 located at a spacing, D, away from reflecting surface 113 along the axial length of the test chamber 116.

As discussed in the Background, in prior designs, a source of error results from thermal expansion associated with the target. The two-reflector target 116 eliminates this source of error when the two reflector faces are made from a common target piece comprised of a material having a very low coefficient of thermal expansion. Specifically, the reflecting surfaces of the two-reflector target 116 may be made to be physically identical in all respects and made of a material such as Invar© so as to have negligible thermal expansion effects. The relative time delay between the two reflections will then be governed by the distance, 2d, which may be very accurately measured and known.

Sensor 10 is operated in the test gas by first applying an electrical excitation pulse signal to the terminals of transducer 111 causing its piezoelectric transducer element to generate a sound wave pulse in the gas. The electrical excitation pulse is typically a sinusoidal signal having a finite time duration produced by an appropriate signal generator external to the test chamber 116. The frequency of the sinusoidal pulse is adjusted to match the resonance frequency of the transducer 111 and the time duration is adjusted to be sufficiently short that the frequency spectrum of the pulse is approximately equal to or exceeds the operating bandwidth of the transducer 111. With these adjustments of the excitation signal, the sound wave produced in the gas will have the minimum rise time and the fewest number of oscillatory cycles as governed by the bandwidth of the transducer 111. In this regard, the preferred embodiment of the speed of sound sensor 10 will utilize a transducer 111 having a maximum practical bandwidth in order to produce ultrasonic pulses having the shortest practical time duration. For this purpose, piezoceramic transducers designed specifically for efficient acoustical coupling into air or other gases are preferred which have a −6 dB bandwidth in the range of 75–100 percent of the transducer resonance frequency. However, ultrasonic transducers having a −6 dB bandwidth of 40–50 percent of the resonance frequency may be used in sensor 10 to yield satisfactory speed of sound measurements under many operating conditions and accuracy requirements.

The distance, d, separating reflecting surfaces 113 and 114 is adjusted to provide a sound propagation time delay between the two reflected ultrasonic pulses sufficient to prevent the pulses from overlapping in time. For example, to ensure good time separation between the two reflected pulses, the time delay, $\Delta t$, should be about ten times greater than the duration of the pulse. Thus, for an ultrasonic pulse having a frequency f, and a time duration, $\delta$, containing N cycles, i.e., $\delta=N/f$, the distance, d, is, from Equation (2) above, $$d = \frac{V_{gas}\Delta t}{2} = \frac{V_{gas}}{2}\left(\frac{10N}{f}\right) = 5N\lambda \qquad (3)$$

Where $\lambda=V_{gas}/f$=wavelength of the sine wave comprising the pulse signal in the gas under test. As one specific example, if N=3 cycles and the transducer resonance frequency is 500 kHz and the speed of sound in the gas is 1450 ft/sec, the separation distance, d, should be d=5(3)(1450)(12)/(500,000)=0.522 in.

Figure 4:
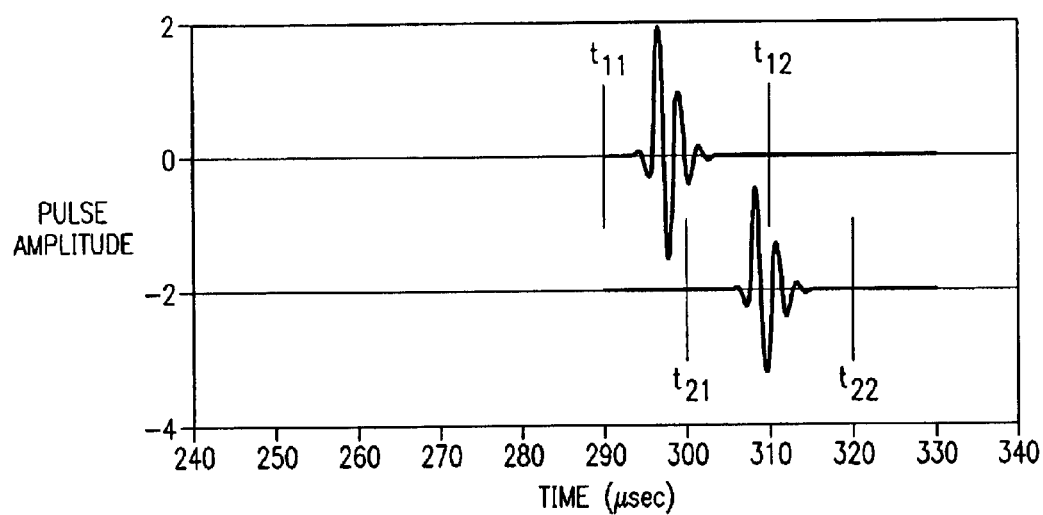
FIG. 4 shows the two reflected pulses separated and having a specified time delay shift preparatory to signal processing.
Figure 5:
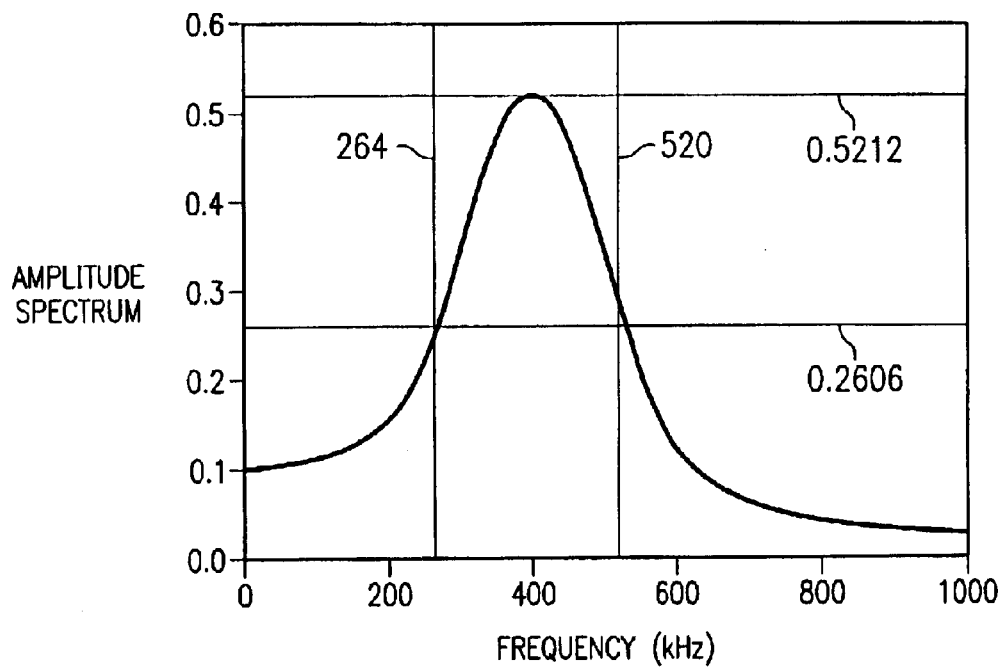
FIG. 5 illustrates the frequency spectrum of the detected ultrasonic pulses.

FIG. 2 shows a sketch of the excitation pulse applied to the transmit-receive transducer 111. FIG. 3 shows two sequential reflected ultrasonic pulses detected by the transducer 111. Also shown in FIG. 3 are time windows, defined by times $t_{11}$ to $t_{12}$ and $t_{21}$ to $t_{22}$, adjusted to bracket the first and second reflection pulses as a preparatory step in separating the pulses for time delay analysis. FIG. 4 shows the two reflected signals after separation illustrating a predetermined shift of the two-way reflection time delay between the pulses. FIG. 5 illustrates the relatively wide bandwidth of the frequency spectra of the reflected pulses. This relatively wide bandwidth is inherently associated with the relatively short time duration of the ultrasonic pulses and is an important characteristic of the invention for accurately determining the time delay between the two pulses.

Figure 6:
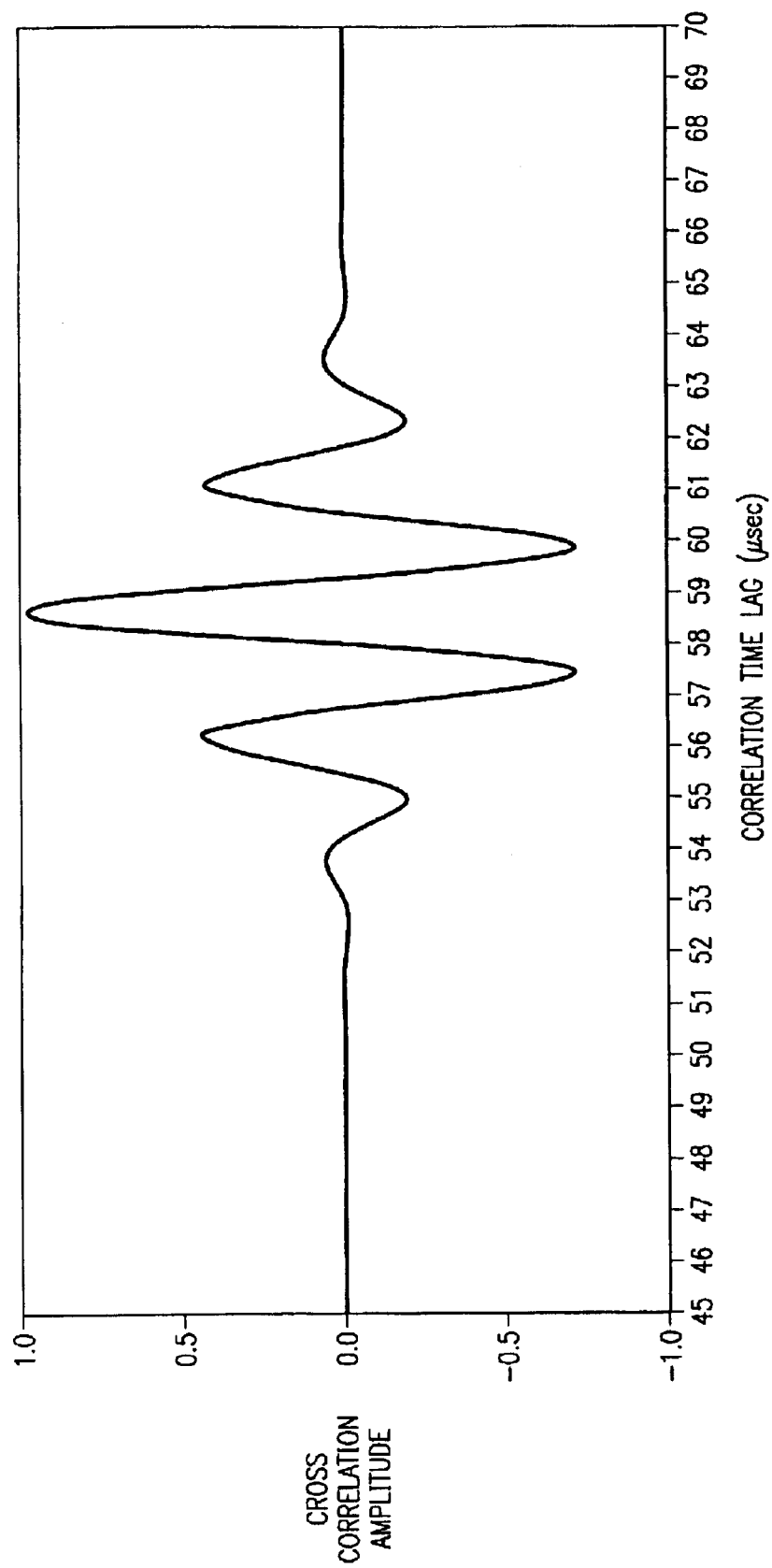
FIG. 6 illustrates the results of cross correlating the reflected pulses of FIG. 3.

FIG. 4 shows the two reflected pulse signals after separation by selecting them in their respective time windows shown in FIG. 3 to form two time-series pulse waveforms. FIG. 4 also shows the earlier arriving pulse to be shifted in time toward the later arriving pulse by a selected precisely known time delay which, as further described below, facilitates determining their separation in time. The received ultrasonic pulse waveforms are digitally sampled at very short time intervals to provide a very high time resolution of the waveforms. To derive the time delay between the pulses from these signals, they are processed by cross correlation whereby the first signal is incrementally time shifted and multiplied by the second signal and the product averaged to yield an analytical measure of the coherence or similarity of the two pulses. The cross correlation process is expressed mathematically by $$R_{12}(\tau_m) = \frac{1}{N}\sum_{n=0}^{N} P_1(t_n - \tau_m)P_2(t_n) \qquad (4)$$

where:

$P_1(t)$=discrete-time-sampled pulse signal 1;
$P_2(t)$=discrete-time-sampled pulse signal 2;
$\Delta t_{sample}$=digital sampling time interval;
$\tau_m = m\Delta t_{sample}$=correlation time lag;
$0 \leq m \leq M = (t_{22}-t_{11})/\Delta t_{sample}$; and
$N = t_{22}/\Delta t_{sample}$ FIG. 6 shows a plot of the cross correlation function, $R_{12}(\tau_m)$, calculated for two reflected pulse signals having approximately three oscillation cycles each. The cross correlation function, $R_{12}(\tau)$, has a positive maximum value at a value, $\tau = \tau_{max}$, representing the number of lag steps, $m = m_{peak}$, at which the peak value of $R_{12}(\tau_{max})$, occurs. This time lag corresponds to the time delay, $\Delta t$, between the two reflected ultrasonic pulses and may be resolved to within the nearest time lag interval, $\tau_{max} = m_{peak}\Delta t_{sample}$. Thus, the digital sampling rate used in recording the reflected ultrasonic signals governs the time resolution to which the travel time delay, $\Delta t$, may be determined.

Figure 8:
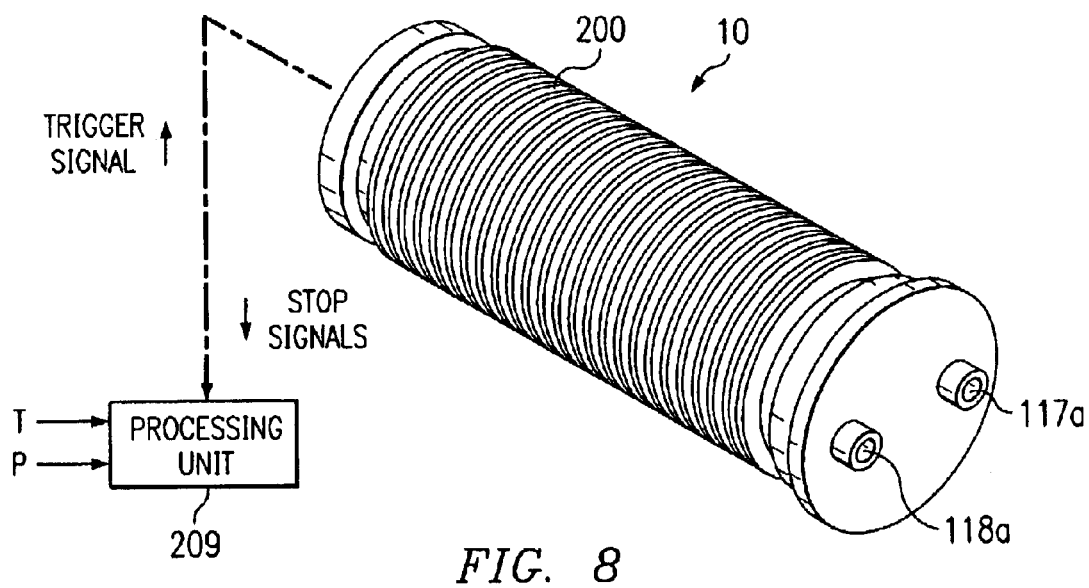
FIG. 8 is a perspective view of the speed of sound sensor.
Figure 7:
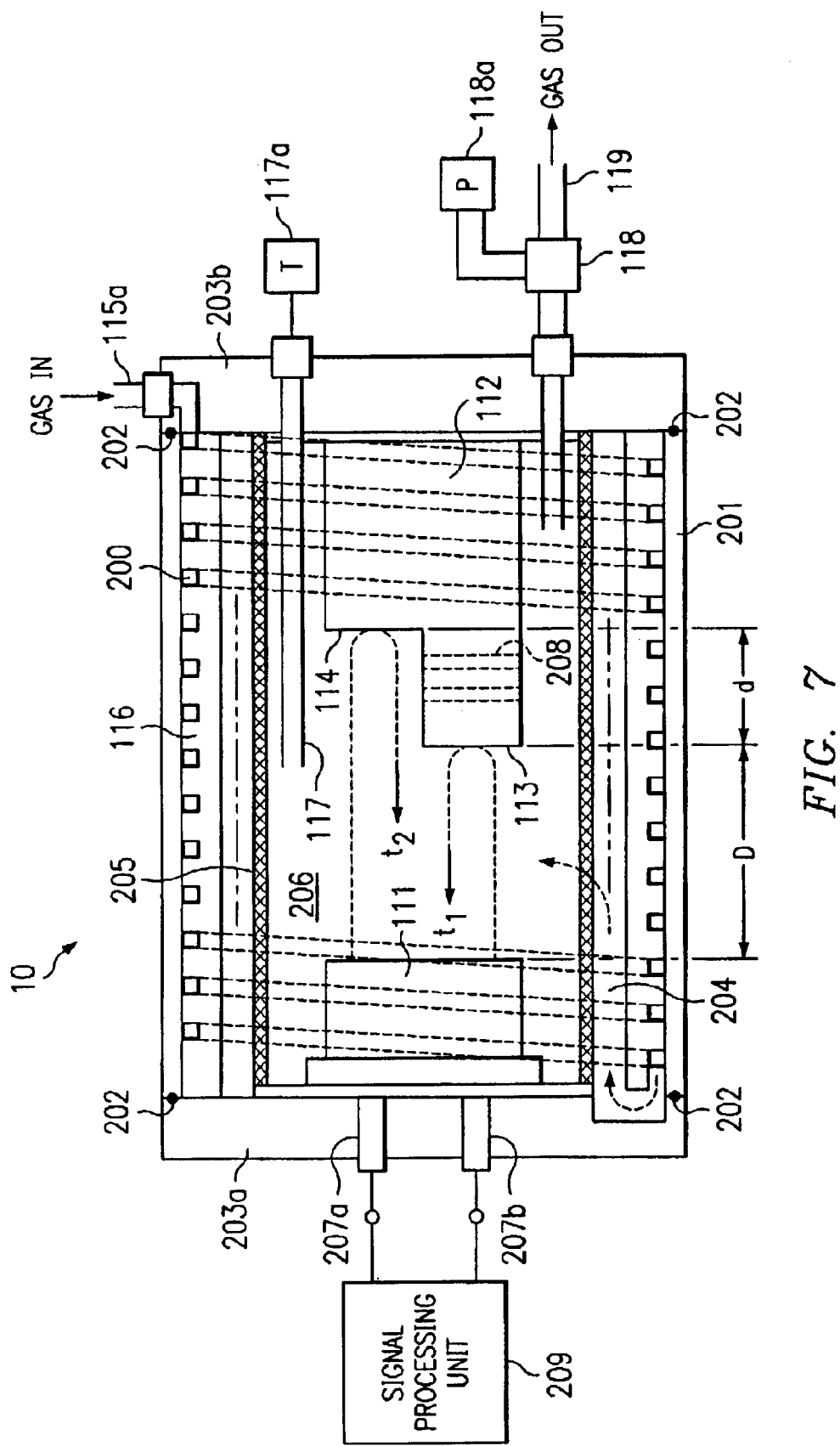
FIG. 7 shows a detailed embodiment of the speed of sound sensor using the two-reflector technique.

FIG. 7 illustrates a more complete drawing of the speed of sound sensor 10 in accordance with the invention. This drawing shows the principal components of sensor 10 described above comprising the test chamber 116, the ultrasonic transmit-receive transducer 111, and the two-reflector target block 112 with reflecting surfaces 113 and 114. FIG. 7 also shows a specific means by which the temperature of the gas to be tested is equilibrated to the temperature of the test chamber 116 prior to entering the speed of sound measurement zone within the chamber 116. FIG. 8 is a perspective view of sensor 10, without an outer housing, illustrating flow channel 200.

A basic principle of operation of sensor 10 is that the thermal mass of the test chamber 116 is used as a heat sink to bring the test gas to the same temperature as chamber 116. This is accomplished on a continuous basis as the gas flows through sensor 10.

More specifically, as shown in FIG. 7, a helical flow channel 200 is arranged around the circumference and along the length of sensor 10. For example, one specific method by which the helical flow channel 200 may be intimately associated with the test chamber 116 is to construct it in the form of a groove, somewhat similar to a screw thread, machined into the outer surface of the cylindrical test chamber 116. This groove is then closed by a close-fitting outer sleeve 201 to form the helical flow channel 200. The outer sleeve 201 is sealed at the chamber end plates 203a and 203b by O-rings 202 so that the entire internal volume of sensor 10, including the helical flow channel 200, will retain the gas pressure. One end plate 203b is arranged to accept gas flowing into inlet 115a and, through an internal path, directs it into the upstream end of the helical flow channel 200. The gas then flows through the helical flow channel 200 and will travel a substantial distance around the chamber 116 until it reaches the opposite end 115b of the flow channel 200 at end plate 203a. The flow rate of the gas is adjusted to a value such that all parcels of gas within the flow channel 200 make moving contact with the sides of the flow channel 200 and, hence, contacts the chamber 116 for a substantial time period. During this time period, the gas will give up or accept heat energy from the chamber 116 so as to equilibrate to the same temperature of the chamber 116 by the time it exits the flow channel 200 at end plate 203a.

An internal path in end plate 203a directs the equilibrated gas into an annular space 204 where it travels freely between the inner wall of the chamber 116 and a porous cylindrical metallic sleeve 205, concentric with chamber 116, through which it diffuses into the speed of sound measurement volume 206 in the inner part of the chamber 116. By traveling through the helical flow channel 200 and diffusing uniformly through the porous metal sleeve 205, the gas is assured to have the same temperature as the chamber 116 and the gas temperature throughout the measurement volume 206 will have uniform temperature.

The use of the porous sleeve 205 minimizes possible streaming flow in the gas transport motions and serves as a final point of intimate contact with the gas for thermal equalization. Sleeve 205 makes the flow more uniform by reducing jetting at the end of the helical flow channel 115b. Another important function of porous sleeve 205 is to provide anechoic conditions within the speed of sound measurement volume 206 in the inner part of chamber 116 by reducing reflections of any ultrasonic waves that contact the sleeve 205. If desired, sleeve 205 may be made from a material that is rough surfaced as well as porous. Essentially, diffuser sleeve 205 serves the function of scattering and absorbing any ultrasonic pulse signals that reverberate within the chamber 116, thereby improving the signal-to-noise ratio of signals received by transducer 111.

Ultrasonic transducer 111 is located in the inner space 206 of chamber 116 at one end of chamber 116. It emits the short duration sound wave pulse whose time of travel between reflecting surfaces 113 and 114 is measured.

An electrical excitation voltage pulse, more specifically a repetitive sequence of triggered pulses having the form of a gated sine wave, is applied to transducer 111. The frequency of the sine wave corresponds to the resonance frequency of the transducer 111. The repetition rate of the transmitted pulses is not critical to the speed of sound measurements. However, this repetition rate is selected so that any possible reverberation within the chamber 116 dies away between successive pulses and, if necessary, is also selected to be sufficiently low that the average power delivered to transducer 111 does not exceed the power rating of transducer 111.

Each applied voltage pulse actuates transducer 111, resulting in an emitted ultrasonic pulse. The ultrasonic pulse travels through the test gas to the opposite end of chamber 116 where it is reflected from surfaces 113 and 114 on target block 112. As explained, below, transducer 111 is a broad bandwidth transducer.

Electrical connections to transducer 111 are brought out of chamber 116 at end plate 203a by means of feedthrough terminals 207a and 207b to maintain the pressure integrity of the chamber 116.

FIG. 7 further illustrates the dual-face structure of target block 112. Target block 112 is of one-piece construction, and is made from a material having a low coefficient of thermal expansion.

Two specific examples of suitable materials for target 112 are Invar® and Super Invar®. Invar® and Super Invar® have thermal expansion coefficients of 1.5E-06 in/in/F and 0.35E-06 in/in/F, respectively. Super Invar® is a well-known steel alloy that exhibits a nearly zero coefficient of thermal expansion. This alloy consists of steel with 32% nickel, 5.5% cobalt, and smaller amounts of other elements for machinability. In reference to target 112, an important concern is dimensional stability when exposed to temperature variations, thus a good choice is Super Invar®.

A suitable construction of target block 112 is two semicircular faces 113 and 114 of a cylinder such that the semicircular faces are oriented parallel to the face of transducer 111. By using the one-piece two-reflector rigid metal target block 112, the derived speed of sound is independent of uncertainties in the effective distance between the local mechanical-acoustical coupling interface between the transducer 111 and the test gas as well as the reflecting surfaces on the target block 112. When made of a low thermal expansion material, the spacing between faces 113 and 114 is essentially independent of temperature and, therefore, the time delay between the pulses reflected at faces 113 and 114 is also essentially independent of temperature.

Gas outlet port 119 is in fluid communication with pressure sensor 118 and 118a and permits the pressure within chamber 116 to be determined. Gas outlet port 119 also permits the gas to exit sensor 10. Small gas flow channels 208 are located in target block 112 to allow the gas near the reflecting surface 114 to more easily move toward outlet port 119.

As an example, the distance, D, between the transducer and the near reflecting surface 113 is approximately 2 inches. A typical distance, d, between the two reflecting surfaces 113 and 114 is 0.500 inch. A typical length dimension of transducer 111 is approximately 1.5 inch. A typical length of target block 112 is 2 inches. Given these dimensions, the remainder of test chamber 116 dimensions would be sized appropriately, resulting in a total length of sensor 10 of approximately 6.5 to 7 inches. A typical diameter of transducer 111 is 1.25 inch and a typical inside diameter of porous sleeve 205 is 1.75 inch. Given these dimensions, the remainder of the chamber 116 diameter, including the helical flow channel 200 groove and the outer sleeve 201 would be sized appropriately, resulting in a total diameter of sensor 10 of approximately 2.5 inches. More specifically, the helical flow channel 200 in chamber 116 may typically have a rectangular cross-section approximately 0.09-inch deep and 0.06-inch wide and a groove-to-groove pitch of 0.125 inch. These dimensions combined with a typical outside diameter of the chamber body 116 of 2.25 inch will result in a total helical flow channel length of approximately 300 inches. At a gas flow rate of 0.2 liter/minute, the dwell time of the gas in this helical flow channel 200 is approximately 8.6 seconds.

The pulse reflections from the target surfaces 113 and 114 return to transducer 111 where, by reciprocal transducer action, they are detected and recorded in digital form. A signal processing unit 209 accepts the digitized pulse waveforms and performs appropriate calculations to determine the difference in travel time, $\Delta t$, between the reflected ultrasonic pulses using the cross correlation method described above in association with Equation (4). Processing unit 209 also receives and records signals representing temperature and pressure from sensor transmitters 117a and 118a.

The distance, $\Delta d$, between the two reflecting faces of target block 112 is very stable with temperature. The speed of sound is derived from the measured time difference, $\Delta t$, between the two detected pulse reflections by the relation involving distance, $\Delta d$, as given by Equation (2) above.

The detected sound wave pulses are digitally sampled and recorded with sufficient time resolution that their times or arrival at the transducer 111 may be measured to within a timing error much less than that associated with the desired accuracy in the derived speed of sound. For example, in order to achieve a speed of sound measured to an accuracy of $\Delta V_{gas} = \pm 0.1$ percent, or less, in a methane-dominated natural gas mixture, the digital sampling rate of the ultrasonic pulse waveforms may be expressed as:

$$f_{sample} \approx \frac{v_{gas}^2}{2d\Delta v_{gas}}$$

For a gas having a speed of sound of $V_{gas}=1,420$ feet/second and a desired measurement precision of 0.50 foot/second, if d=0.500 inch, the digital sampling rate of the received ultrasonic pulse waveform must be, by Equation (5), $f_{sample}= 48.4 \times 10^6$ samples/second.

For most natural gas mixtures, ultrasonic pulses having an operating resonance frequency in the range of 300–500 kHz and a bandwidth of 75–100 percent of the operating resonance frequency are capable of providing ultrasonic pulse-echo signals having acceptable signal-to-noise ratio when using two-way reflection path lengths of about 6 inches, or less. Likewise, ultrasonic pulses in the 300–500 kHz frequency range are capable of providing the desired speed of sound accuracy stated in the above example when their waveforms are sampled and digitized at a sampling rate of $48 \times 10^6$ samples/second. Frequencies and bandwidths outside this range may also be suitable.

Transducer 111 in FIG. 7 is capable of operating with a preferred resonance frequency in the range of 300–500 kHz. Furthermore, transducer 111 has a preferred relatively wide bandwidth in the range of 75–100 percent of its resonance frequency. As described above, such a wide bandwidth characteristic is required for generating short time duration ultrasonic pulses that, in turn, yield a well-defined cross correlation function peak by which the time delay between the reflected pulses is determined.

The overall residual error associated with the above-described speed of sound measurement example, when compared with the theoretical value of the speed of sound in the test gas derived from an accurate analytical equation of state and assuming perfect accuracy in the temperature, pressure, and composition of the gas has been demonstrated to be less than 500 parts per million in a variety of laboratory tests. This error is a result of random residual errors related to the experimentally measured gas pressure, the experimentally measured gas temperature, uncertainties in the gas composition, spatial variations in the homogeneity of the gas in the test chamber, the digital sampling resolution of the ultrasonic pulses, the signal-to-noise ratio of the recorded sound pulses, and the computational accuracy of the cross correlation time lag between the two recorded sound pulses.

Other Embodiments

Many variations and modifications may be made to the disclosed embodiments of the invention without departing from the spirit and principles described herein. All such modifications and variations are intended to be included within the scope of the present invention, as defined by the following claims.

What is claimed is:

1. A transit time speed of sound sensor for gaseous media, comprising:
   a helical channel having a generally cylindrical shape, such that it encloses an inner chamber;
   end pieces at each end of the inner chamber, such that the inner chamber may contain the gas to be tested;
   a gas input port operable to receive a flow of gas into the helical channel;
   wherein the helical channel is arranged such that gas may enter the helical channel, flow through the helical channel, and enter the inner chamber;
   a dual-faced target at one end of the chamber;
   a transducer at the opposing end of the chamber, the transducer operable to produce an ultrasonic pulse in the gas and to receive a reflection of the pulse from each face of the target; and
   a gas output port operable to exhaust gas from the chamber.

2. The sensor of claim 1, further comprising a porous diffuser sleeve enclosing the inner chamber volume of the sensor, such that the gas may exit the helical channel, enter a space between the inside wall of the chamber and the diffuser sleeve, and enter the inner chamber through the diffuser sleeve.

3. The sensor of claim 1, wherein the dual-face target is made from a single piece of material.

4. The sensor of claim 1, wherein the target is made from a material having a low thermal expansion.

5. The sensor of claim 1, further comprising a temperature sensor within the chamber.

6. The sensor of claim 1, further comprising a pressure sensor within the chamber.

7. The sensor of claim 1, wherein the transducer has an operating resonance frequency in the range of 300–500 kilohertz.

8. The sensor of claim 7, wherein the transducer has a bandwidth of between 75–100 percent of its operating resonance frequency.

9. The sensor of claim 1, further comprising an outer sleeve enclosing the helical channel.

10. The sensor of claim 1, further comprising a processing unit, operable to receive signals representing pulses reflected from each face of the target, and to cross correlate the reflected pulses.

11. A transit time speed of sound sensor, comprising:
    a helical channel having a generally cylindrical shape;
    a gas input port operable to receive a flow of gas into the helical channel;
    a porous diffuser sleeve enclosing an inner volume of the gas test chamber of the sensor;
    end pieces at each end of the inner chamber, such that the inner chamber may contain the gas;
    wherein the helical channel and diffuser sleeve are arranged such that gas may enter the helical channel, flow through the helical channel, enter a space between the inside wall of the chamber and the diffuser sleeve, and enter the chamber through the diffuser sleeve;
    a dual faced target at one end of the chamber;
    a transducer at the opposing end of the chamber, the transducer operable to deliver an ultrasonic pulse and to receive a reflection of the pulse from each face of the target; and
    a gas output port operable to exhaust gas from the sensor.

12. A method of measuring the speed of sound of a gas in a chamber, comprising the steps of:
    receiving the gas into a helical channel surrounding the chamber;
    flowing the gas through the helical channel until it reaches a temperature substantially the same as that inside the chamber;
    receiving the gas into the chamber;
    transmitting an ultrasonic pulse from one end of the chamber, directed toward the opposing end of the chamber;
    reflecting the pulse from a first face of a target;
    reflecting the pulse from a second face of a target, the second face being a known distance farther from the transducer than the first face; and
    receiving the reflected pulses.

13. The method of claim 12, wherein the step of receiving the gas into the chamber is performed by diffusing the gas through a porous material separating the helical flow channel coil and the inner volume of the chamber.

14. The method of claim 12, wherein the target is fabricated from a single piece of material.

15. The method of claim 12, wherein the target is made from a low thermal expansion material.

16. The method of claim 12, further comprising the step of cross correlating the reflected pulses.

17. The method of claim 12, wherein the transducer has an operating resonance in the range of 300–500 kilohertz.

18. The method of claim 17, wherein the transducer has a bandwidth of between 75–100 percent of its operating resonance frequency.

* * * * *